United States Patent [19]

Loo et al.

[11] Patent Number: 5,127,904
[45] Date of Patent: * Jul. 7, 1992

[54] IMPROVED NEEDLE-LESS PARENTERAL FLUID INJECTOR

[76] Inventors: George D. H. Loo, 9814 Curwood Pl., Beverly Hills, Calif. 90210; Gordon A. Wong, 118 Northlite Cir., Sacramento, Calif. 95831

[*] Notice: The portion of the term of this patent subsequent to Aug. 20, 2008 has been disclaimed.

[21] Appl. No.: 503,278

[22] Filed: Apr. 2, 1990

Related U.S. Application Data

[63] Continuation-in-part of Ser. No. 231,090, Aug. 11, 1988, abandoned.

[51] Int. Cl.⁵ .............................................. A61M 5/00
[52] U.S. Cl. ........................................ 604/83; 604/247; 137/533; 251/149.6
[58] Field of Search ..................... 604/33, 80, 81, 82, 604/83, 84, 122, 123, 124, 125, 247, 249; 251/149.6, 149.7; 137/533, 614.2

[56] References Cited

U.S. PATENT DOCUMENTS

| 4,005,710 | 2/1977 | Zeddies et al. | 137/533 |
| 4,324,239 | 4/1982 | Gordon et al. | 604/122 |

Primary Examiner—C. Fred Rosenbaum
Assistant Examiner—William H. Lewis
Attorney, Agent, or Firm—Limbach & Limbach

[57] ABSTRACT

A fluid injector for use with a needle-less syringe or needle-less add-on IV line is disclosed. The injector is connected to a main IV line and has a fluid passageway from the syringe or the add-on IV set to the main IV line. The injector comprises an anti-backflow valve member where the member is movable under fluid pressure along between a first position where the fluid cannot flow through the injector and a second position where the fluid can flow through the injector. The member is a sinking type and has a specific gravity greater than 1.0. The injector also comprises a valve located near the syringe end of the injector for receiving the fluid from the syringe or the add-on IV line for injection into the main IV line and for automatically preventing air embolus entering into the IV line. The anti-air embolus valve comprises a piston in a conduit. The piston is movable between a first position and a second position. The piston has a central bore for the passage of the fluid, a capped end and an inlet end. An envelope surrounds the piston and is interior to the conduit, between the capped end and the inlet end. The anti-air embolus valve also has a stainless steel spring, surrounding the piston in the envelope to maintain the piston in the first position, where fluid and air cannot flow. An o-ring surrounds the piston at the capped end and forms a seal to prevent air and fluid flow through the injector in the first position.

17 Claims, 7 Drawing Sheets

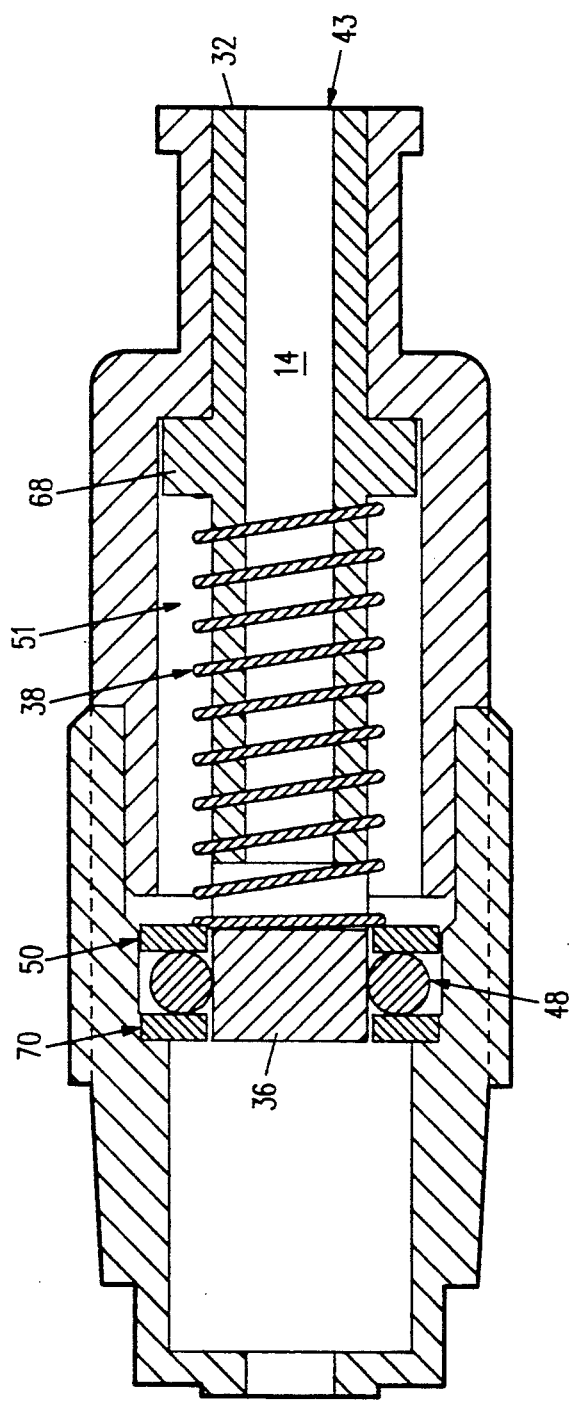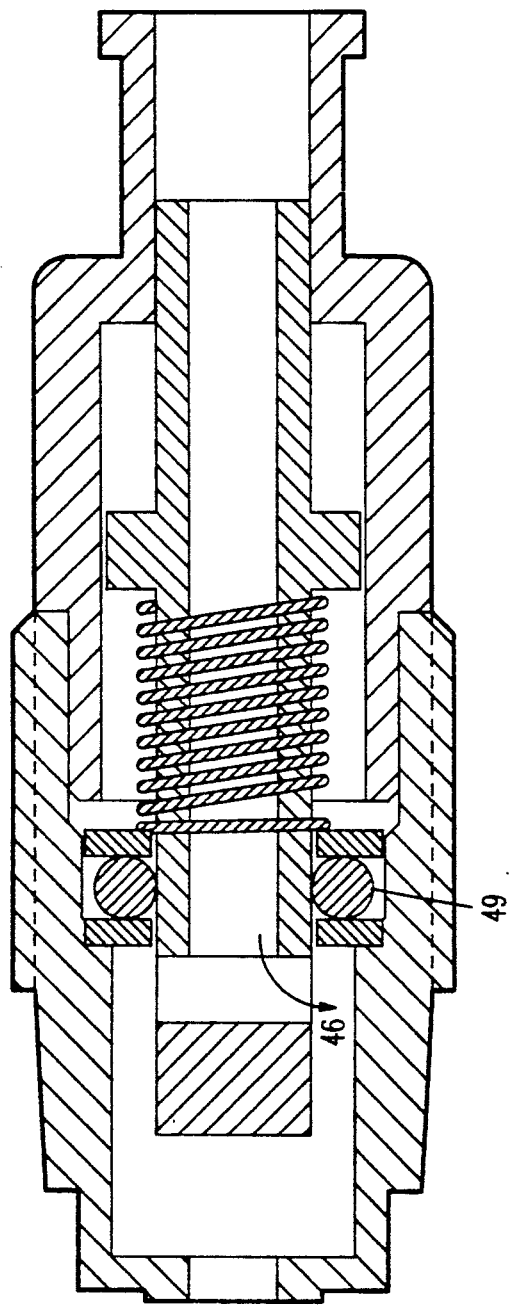
FIG. 3a
FIG. 3b

IMPROVED NEEDLE-LESS PARENTERAL FLUID INJECTOR

This is a continuation-in-part application of a co-pending application Ser. No. 07/231,090, filed on Aug. 11, 1988 now abandoned.

TECHNICAL BACKGROUND

The present invention relates to an improved needle-less parenteral fluid injector which is more efficient and is safer for both the health-care worker as well as the patient.

BACKGROUND OF THE INVENTION

In the health care profession, intravenous injection of fluids and drugs are routinely administered. A typical application is in the surgical field where anesthetics, such as barbiturates, sedatives, and narcotics are usually administered to a patient who has an intravenous (IV) line attached. Thus, in a typical surgical procedure, at various times, or at any one time, a number of different drugs or fluids must be administered to the patient.

Typically in anesthesia, medications are given on a "when needed basis". This varies with different patients, depending upon factors such as age, weight, sex, medical disease and individual metabolism. When medications are needed, they are usually administered on the basis of "the sooner the better". In the prior art, the method of administering medications to a patient through an IV line is performed in the following five steps (assuming that the fluid or medication is already in a needled syringe): (1) uncap the needle on the syringe; (2) rapidly, but carefully, insert the needle into a rubber plug port in the IV line; (3) inject the medication; (4) withdraw the needle from the rubber plug port; (5) carefully recap the needle to preserve sterility and to protect the health care worker from a source of accidental skin puncture from a possible blood-borne-disease contaminated needle. Needle sticks have been the most frequently reported injury to health care workers in American hospitals. Recently the Center For Disease Control in Atlanta, Ga., has recommended that anesthesiologists and nurses avoid recapping of needles after using them for injection into an IV line. This is to avoid exposing themselves to a risk of contracting contagious blood-borne diseases, such as AIDS, Hepatitis, etc., through accidental needle puncture when the needle on the syringe is recapped.

Guaiac testing, for occult blood, has shown the presence of blood in IV lines even though no blood was grossly visible, and the IV flow was considered to be anterograde at all times. Thus, IV fluid connected to any patient may contain infectious blood even though no blood is grossly visible. The possibility of accidental needle puncture with a potentially contaminated needle occurs twice during each normal intravenous injection. The first occurs when the needle is being inserted into the rubber plug port in the IV line. The second time, is when the needle is recapped after use.

During the course of an anesthetic treatment, many repeated, intermittent intravenous injections of medications and fluids are necessary. Thus, the number of times of potential exposure to a possibly contaminated needle puncture is manifold. In response to the Center For Disease Control findings and recommendations, many institutions, such as the University of California Hospitals in San Francisco, are recommending to their health care workers that needles should not be routinely recapped after use for intravenous injections. While this removes one problem associated with the present method, many other problems, such as efficiency of administering of the medication, still remain.

In the prior art, a number of needle-less fluid injection apparatuses are disclosed. For example, see U.S. Pat. Nos. 3,994,293; 2,886,457; 3,416,567; 4,506,691; 4,585,435; 4,737,145; and 4,015,336. However, none of the references teaches or suggests an apparatus for IV injections which is safe for the patient in that the apparatus provides for an automatic anti-backflow valve and an anti-air embolus valve and simultaneously permits administration of multiple medications both by IV gravity drip and pressure infusion.

SUMMARY OF THE INVENTION

In the present invention, a parenteral fluid and medication injector is disclosed. The injector has a fluid transport means with one end for connecting to a patient and a fluid input port for receiving a fluid. The injector comprises a fluid conduit having two ends. A first end of the fluid conduit receives the fluid with the second end having means to connect to the fluid input port of the fluid transport means. An anti-backflow valve member is in the fluid conduit near the second end for preventing the backflow of the fluid. A valve means is provided located at the first end of the fluid conduit for preventing air embolus in the fluid conduit. The valve means has an injection piston with a central bore for the passage of the fluid. The injection piston is in the fluid conduit and is movable between a first position and a second position with a spring urging the piston in the first position. The piston has a capped end and an injection inlet port and an envelope surrounding the piston interior to the fluid conduit and between the capped end and the injection inlet port. A seal is provided between the piston and the fluid conduit at the capped end for sealing the fluid between the inlet port and the fluid transport when the piston is in the first position. The valve further has means for permitting fluid flow between the inlet port and the fluid transport when the piston is in the second position. Finally, fluid is permitted to flow between the inlet port and the envelope.

BRIEF DESCRIPTION OF THE DRAWINGS

FIG. 3a and 3b are cross-sectional views of portions of the injector shown in FIG. 2.

DETAILED DESCRIPTION OF THE DRAWINGS

Figure 1:
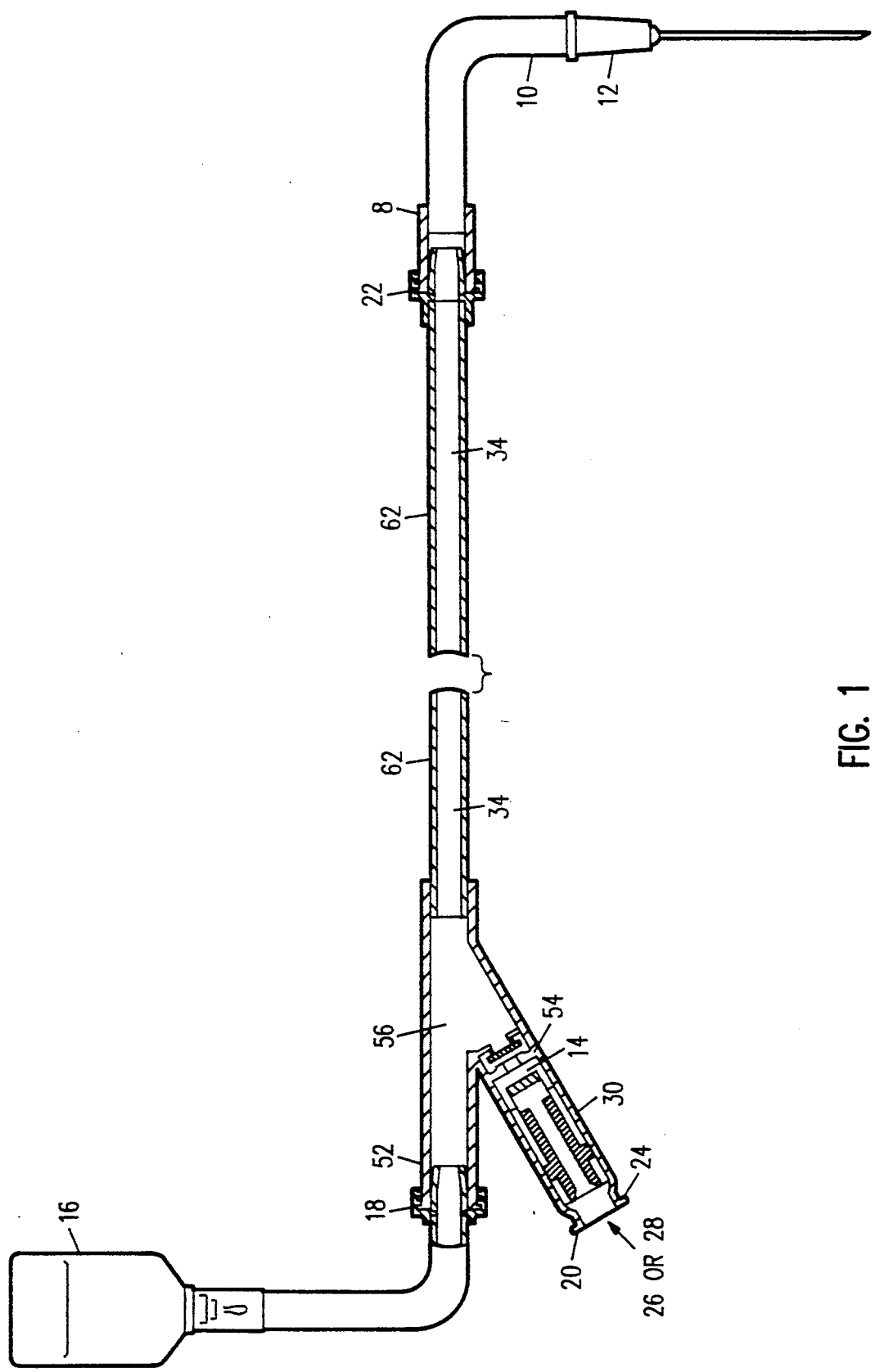
FIG. 1 is a schematic partial cross-sectional view of one embodiment of the parenteral fluid injector of the present invention for use with an intravenous (IV) line.

Referring to FIG. 1 there is shown a parenteral fluid injector 20 of the present invention for use interposed in an IV line 10. The IV line 10 has one end having a needle 12 attached thereto for connection to a patient. The IV line 10 also has another end 8 which is a fluid input port for receiving a fluid from the injector 20. The IV line 10 has another end 18 which is a fluid output port for inputting fluid from IV bottle 16 into a female luer lock connector 52 of injector 20. The injector 20 has a male luer end 22 which is connected to the fluid input port 8 of the IV line 10. The male luer end 22 is connected to a Y-shaped chamber 56 by a variable length of flexible tubing or rigid conduit 62. The parenteral fluid injector 20 has another end 24 which is adapted to receive a needle-less syringe 26 or a needle-less add-on IV line tip connector 28 which delivers fluid into the injector 20, then into the IV flow stream 14 and into 34 and then into the IV line 10. Injector body 30 of the parenteral fluid injector 20 of the present invention has an outflow end 54 connecting injector valve body 30 to IV stream 34. The Y-shaped chamber 56 of the injector 20 connects fluid channels from connector 22, connector 52 and connector 24 of the parenteral fluid injector 20.

Figure 1A:
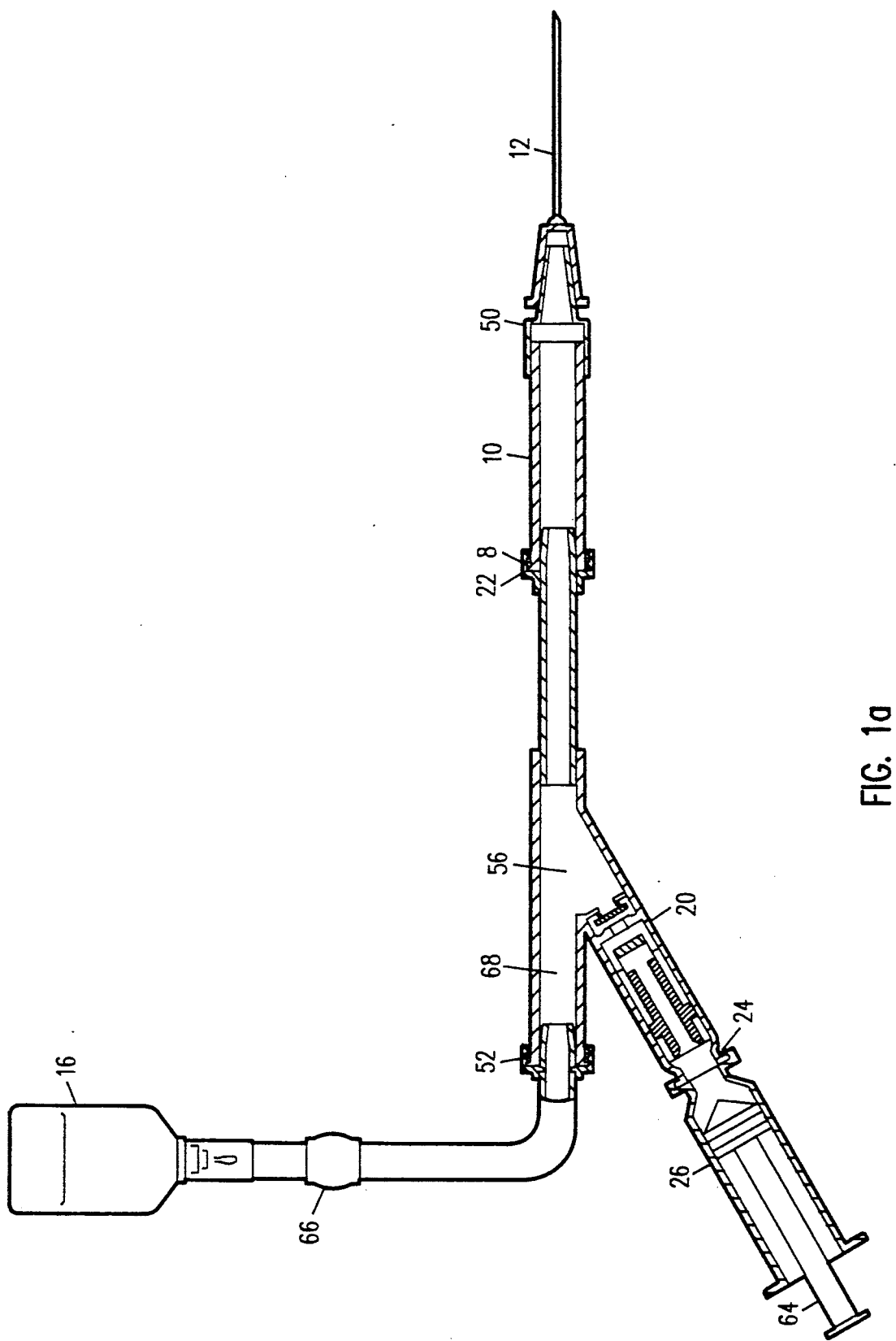
FIG. 1a is a schematic partial cross-sectional view of the parenteral fluid injector shown in FIG. 1 when used with a syringe device.

Referring to FIG. 1a there is shown a schematic partial cross-sectional view of parenteral fluid injector 20 of the present invention when attached to a needle-less syringe 26 of any capacity. The plunger 64 of the syringe 26 may be pushed manually by hand or by a programmed electronic infusion pump to inject a precise medication dose at any instant. Fluid flow is from syringe 26, through injector 20, through fluid Y-shaped chamber 56, through male luer connector 22, through connector 8, and into IV tubing 10 going into needle 12 in patient. Normally, when used in surgery, IV tubing 10 contains a built in check valve 66 to prevent backflow of syringe 26 contents from flowing towards IV bottle 16 during rapid injection of medication. When used with an IV tubing set not containing a check valve 66, tubing 10 would be pinched off manually or closed temporarily using a prior art roller clamp, between connector 52 and IV bottle 16, during rapid injection, and then released. In another embodiment of the parenteral fluid injector of the present invention, another anti-backflow valve similar to the anti-backflow valve 42 of the injector 20, as shown in FIG. 2, would be built into injector 20 at position 68 as shown on FIG. 1a.

Figure 1B:
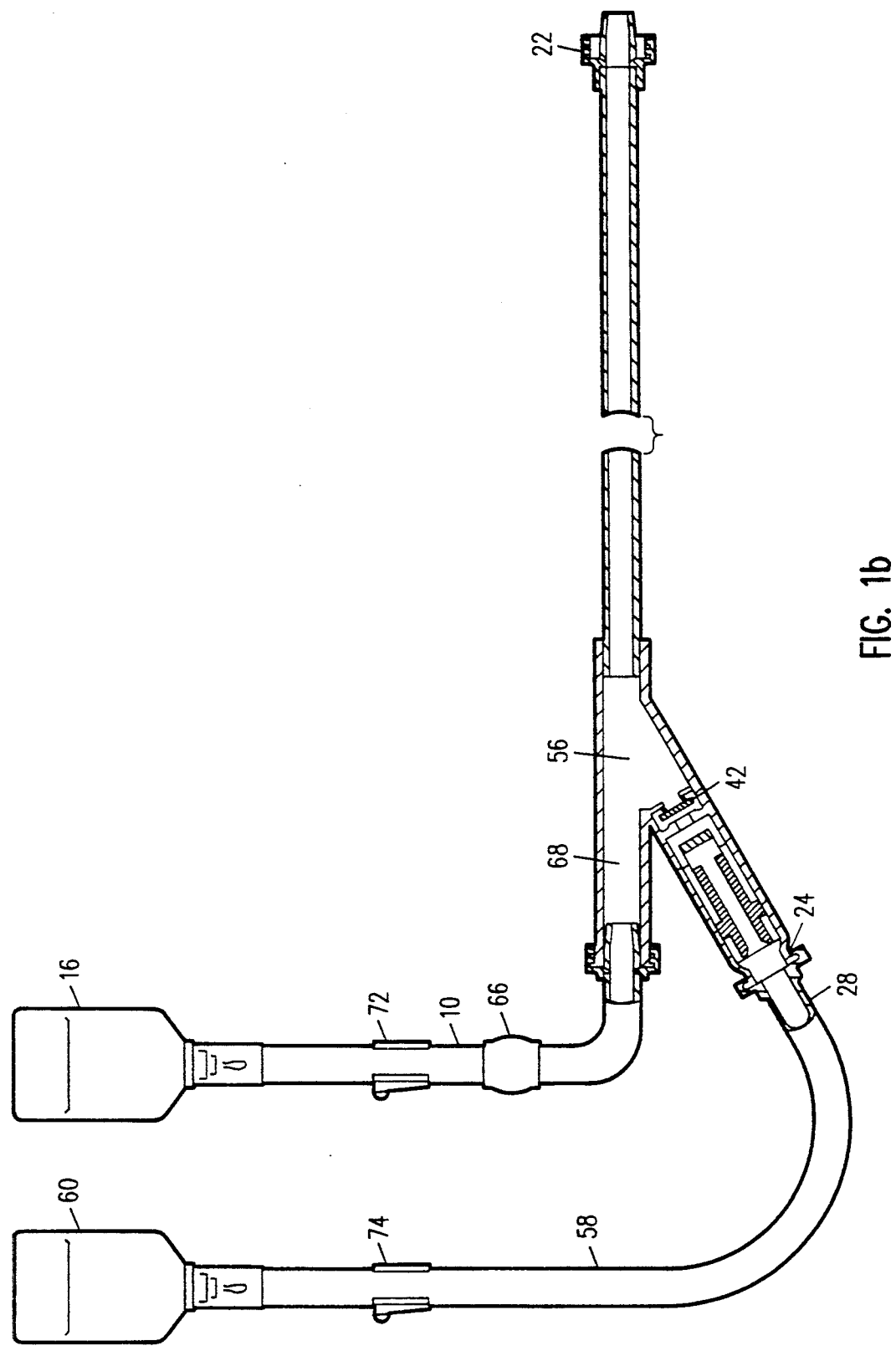
FIG. 1b is a schematic partial cross-sectional view of the parenteral fluid injector shown in FIG. 1 when used with a secondary or add-on IV set.

Referring to FIG. 1b there is shown a schematic partial cross-sectional view of a parenteral fluid injector 20 of the present invention when attached to a needleless tip 28 of an add-on (or piggy-back) IV tubing 58 connected to IV fluid container 60 on one end and to female luer lock connector 24 on the other end. In this configuration of use of the parenteral fluid injector of the present invention, both IV line 10 and IV line 58 can be run simultaneously. As will be explained, there will be no backflow into either IV tube 58 or IV tube 10 because of the valve 42 and valve 66. Gravity drip of IV fluid is possible simultaneously from IV bottle 16 and IV bottle 60

Figure 2:
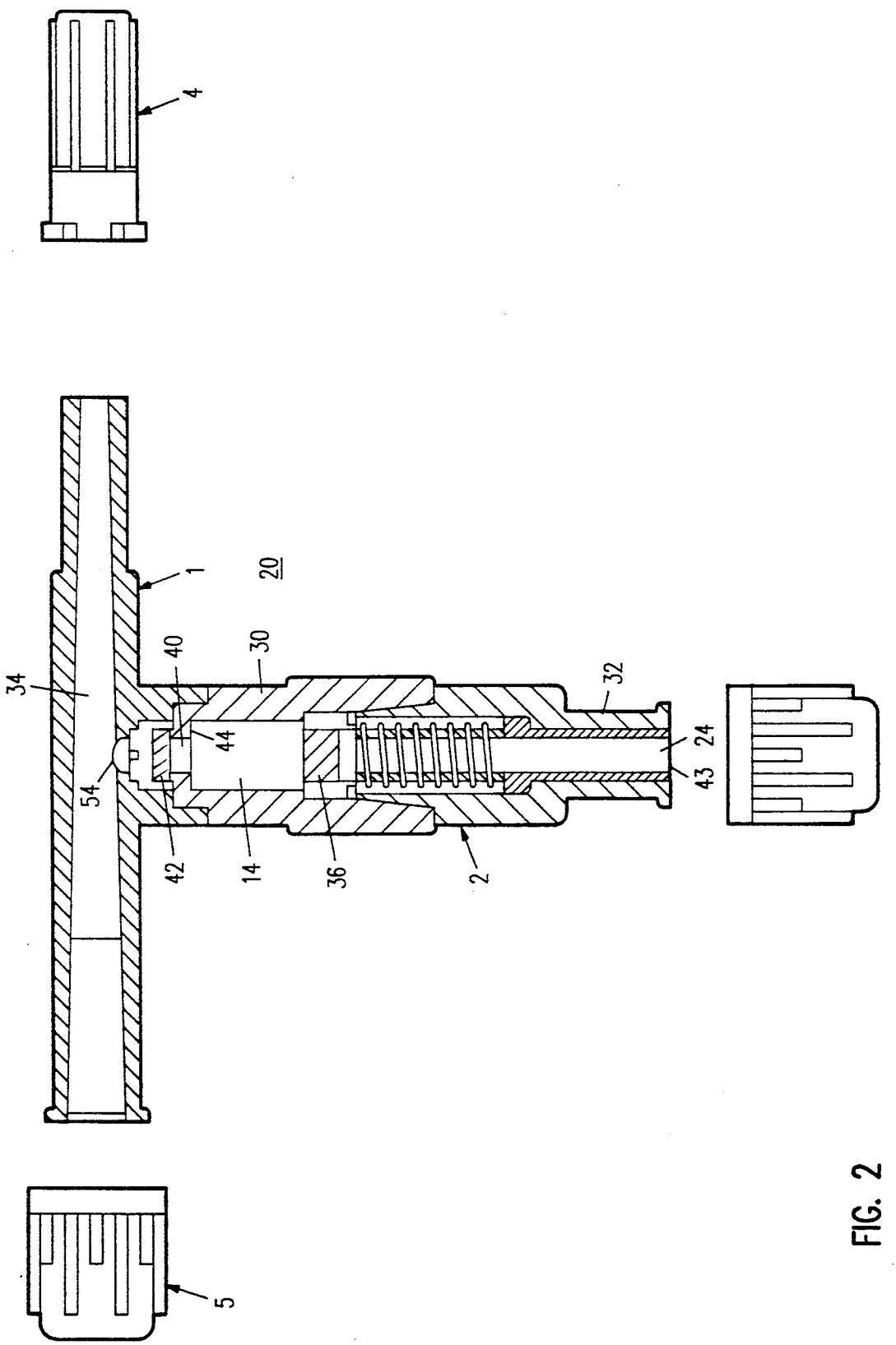
FIG. 2 is a cross-sectional view of the injector of the present invention shown in FIG. 1.

Referring to FIG. 2 there is shown in greater detail one embodiment for the parenteral fluid injector 20 of the present invention. The injector 20 comprises a barrel shaped member 30 with a central fluid passage 14 therebetween. Near one end 54 of the injector 20 is an anti-backflow valve member 42. The anti-backflow valve member 42 in this embodiment is a disc-shaped member. Any other type of anti-backflow valve may also be used. The valve member 42 is movable between a first position and a second position. In the first position, the valve member 42 covers the aperture 40 which is in the fluid passageway 14 and prevents the flow of fluid from the one end 54 to the other end 24. In the second position, the valve member 42 comes to rest against a stop 44. Stop 44 may be built on as a part of the injector chamber 30 or it may be built on as part of disc member 42. However, the fluid flow in passageway 34 from the other end 24 to the one end 54 is maintained as the fluid flows around the disc 42 and to the one end 54.

The valve member 42 is movable between the first position and the second position only by the difference in the pressure of the fluid from one side of the valve member 42 to the other side of the valve member 42. Thus, any pressure differential on the two sides of the valve member 42 causes the valve member 42 to move to the side of lower pressure. However, in normal operation, the injector 20 is positioned in an upright position with the one end 54 above the other end 24. Further, the valve member 42 has a specific gravity greater than 1.0, such that when the injector 20 is in the upright position, the valve member 42 covers the aperture 40. Even if there is fluid in the passage 34 and 14, because the specific gravity of the member 42 is greater than 1.0, the member 42 will "sink" with the injector 20 in the upright position and cover the aperture 40.

The injector 20 further comprises a piston-shaped member 32. The piston-shaped member 32 has a central bore which contains the fluid passageway 14. The piston 32 has a capped end 36 and an injection inlet port 43. The fluid passageway 14 receives fluid from the syringe 26 in a direction parallel to the axis of the piston 32. Near the capped end 36, the passageway 14 flows in a radial fluid passage 46 (see FIG. 3b).

The piston 32 is movable between a first or closed position and a second or open position. When the piston is in the first position, the capped end 36 is immediately adjacent to and abuts an o-ring 48 which in turn is immediately adjacent to and abuts a ring retainer collar 70 built onto the cylindrical outer member 30. Thus, when the piston 32 is in the first or closed position, atmospheric air from end 24, or fluid from end 54 in fluid path 34 is prevented from flowing from one end of the injector 20 to the other end. The piston 32 is maintained in the first position by the stainless steel spring 38, or any other type of spring device, which urges against the piston 32 to maintain it in the first position. The stainless steel spring 38 rests against spring stop 68, which is a circular flange about the piston 32. The spring 38 is wound about the piston 32 in an envelope space 51 which surrounds the piston 32, exterior thereto, but interior to the chamber 30.

The piston 32 is moved into the second or open position when the needle-less tip of the syringe 26 or the needle-less tip of an IV line 28 (FIG. 1b) is pushed into the other end 24 of the injector 20 and is mated to the injection inlet port 43 of the piston 32. Thereafter, the syringe is locked with the female luer lock connector 24, thereby maintaining the piston 32 in the second or open position. In the second position, the spring stop 68 of the piston 32 is urged against stainless steel spring 38. The spring 38 is pushed against a washer 50, which compresses the o-ring 48. In one embodiment, the o-ring 48 has an outer diameter smaller than the diameter of the chamber 30 and an inner diameter substantially smaller than the diameter of the piston 32 (when the o-ring 48 is not expanded and placed about the piston 32). The o-ring 48 is expanded and is placed about the piston 32. Since the inner diameter of the o-ring 48 is smaller than the diameter of the piston 32, the expansion of the o-ring 48 forms a seal of the o-ring 48 with the diameter of the piston 32. When the o-ring 48 is so compressed, the front face 49 is squeezed against the ring collar retainer 70, with the result that in both the first and the second position, the inner diameter of the o-ring 48 forms a seal with the side of the piston 32, and the front face 49 of o-ring 48 forms a seal against the adjacent face of ring retainer collar 70. This forms the important seal for the anti-air embolus component of the injector 20 of the present invention. The outer diameter of o-ring 48 is not used to form a seal in the injector 20, because doing so would cause great friction for the piston 32 to move against, especially from the second position back to the first position. The anti-air embolus mechanism would not be as reliable as it is in the injector 20 of the present invention. This is because compressing an o-ring from the front to the back, while it is restricted on it's outer diameter, causes the material of the o-ring 48 to be pushed towards the inner diameter, thus decreasing the inner diameter and increasing friction. In the second position, the capped end 36 is pushed away from the o-ring 48, exposing the radial passage 46. This then permits fluid or medication to flow from the injection inlet port 43 to the one end 54 of the injector 20, past the anti-backflow valve member 42, and into the IV fluid tubing 10, and thus into the patient.

The operation of the parenteral fluid injector 20 of the present invention is as follows: Initially, a needleless IV tubing 10 with an end 18 is connected onto a female luer lock connector 52 of the injector 20. Male luer end 22 of the injector 20 is connected to the fluid input port 8 of the IV line 10. Once the fluid from the IV bottle 16 flows through the line 10 and through the passageway 34, through the luer connector 22, and through the tubing 10, the remainder of the injector 20 is primed with IV fluid, using a syringe, to expel all of the residual air in the system.

Priming of the injector 20 is done as follows: a fluid filled syringe 26 is attached to the inlet 24 of the injector 20. In the normal operational position, where the one end 54 is above the other end 24, fluid is injected to displace air through the piston 32 inside passageway 14, past disk member 42, to join the fluid in flow path 34. Next, the syringe with attached injector 20 and chamber 30 is turned "upside down" such that the other end 24 is above the one end 54. A negative pressure is then applied to the injector 20 and chamber 30 by pulling back strongly on the plunger of the fluid filled syringe 26. This causes a differential in pressure between the two sides of the anti-backflow valve member 42 causing it to move to the first position, closing off the aperture 40. This sealing of aperture 40 prevents fluid in passageway 34 from backflowing and entering the injector 20. Since there is no seal between the spring stop 68 and the wall of the outer chamber 30, air in the unprimed envelope space 51 which surrounds the piston 32, and spring 38, exterior thereto, but interior to chamber 30, escapes between the stop 68 and the wall 30, and through the inlet port 43 of the piston and is thus aspirated upwards into the syringe 26. The air, being lighter than water or fluid, travels upwards to the top of the syringe 26, and as the plunger of the syringe 26 is released, the fluid in the bottom of the syringe flows downwards into the injector 20 to replace the air that surrounded the piston 32 and spring 38 in envelope space 51. Once the injector 20 is so primed, the syringe 26 is removed. The injector 20 is then returned to the normal position where the one end 54 is "above" the other end 24. The primed injector 20 can now be connected with another needleless syringe 26 containing medication, or with a needle-less add-on IV line 28, or it may be covered with a sterile cap 2 (FIG. 2) until the primed injector 20 is used for infusion. Once the entire IV system is filled with fluid and the injector 20 is primed, the IV tubing 10 can be connected to the needle 12 connected to the patient.

In the normal position where the one end 54 is "above" the other end 24, a syringe 26 can be left in place. Since no pressure is applied to the syringe 26 and since the needle 12 is typically connected to a vein of a patient where there is a source for fluid pressure (IV fluid column hydrostatic pressure), there is a pressure differential between the two sides of the anti-backflow valve member 42. Further, as previously stated, in the normal position where the valve member 42 has a specific gravity of greater than 1.0, the valve member 42 returns to the position closing off the aperture 40. Thus, the valve 42 would prevent any fluid from the IV line 10 to flow back into the injector 20. Further, with the valve 42 over the aperture 40, closing off fluid pressure to the chamber 56, atmospheric pressure would keep the fluid in the envelope 52 from flowing out — not withstanding the absence of a seal between the spring stop 68 and the outer diameter 30. This is analogous to sealing the top end of a capillary tube filled with fluid, with the bottom end open and the fluid remaining in the tube.

The advantage of a single o-ring 48 sealing the piston 32 to the chamber 30 is that the piston 32 has to overcome less sealing friction. In addition, with the o-ring 48 having an outer diameter less than the chamber 30, the piston 32 has to overcome even less friction during motion. Thus, the piston 32 is easier to operate and the injector 20 is more reliable and thus safer for patients. Further, with only one seal, the envelope 52 can be primed with fluid thereby assuring that no air will be anywhere in the injector 20. Without the presence of any air, even a seal failure, cannot cause air to be inadvertently injected into the patient from the injector 20. Thus, the injector 20 of the present invention provides for a high degree of safety.

In this manner, the syringe 26 may be left virtually indefinitely connected to the injector 20 without any fear of backflow of fluid from the IV line 10 entering into the syringe 26 and diluting the medication contained therein. In this position, the syringe 26 may be left and applied "on demand". Further, when pressure is applied to the syringe 26, the fluid would flow through the passageway 34 and into the IV line 10. When it is desired to change the syringe 26 to another syringe that contains different fluid or medication, the syringe 26 is simply removed from the female luer lock connector 24. When syringe 26 is so removed, the piston 32 is automatically retracted into the first position where by the capped end 36 abuts the o-ring 48 and seals the passageway 34. Sealing of the passageway 34 prevents air embolus from entering into the IV line 10 and into the patient.

As can be seen from the foregoing, there are many advantages to the injector 20 of the present invention. First and foremost is that no needles are used (except initially when the needle 12 or the IV catheter 12 is inserted into the patient for connection to the IV line 10). Secondly, the syringe 26 can be left virtually indefinitely connected to the IV line 10 without any fear of back flow of fluid from the IV line 10 into the syringe 26. Thus the syringe 26 can be maintained on line and drugs will be ready to be administered on an immediate "as-needed basis". Any pressure increase in the primary IV line causes the anti-back flow valve to close off the flow of fluids from the secondary line. Thirdly, the injector 20 permits both gravity IV drip and pressure infusion techniques because once the piston 32 is moved to the second or open position by attaching needle-less syringe tip 26 or needle-less add-on IV line 28 to the injector 20, the fluid flow path from path 14 to path 34 is open and offers no resistance to flow. Finally, and most importantly, the injector 20 of the present invention automatically prevents the introduction of air embolus into the IV line 10, and thus into the patient, when the syringe 26 is removed or exchanged.

Figure 4:
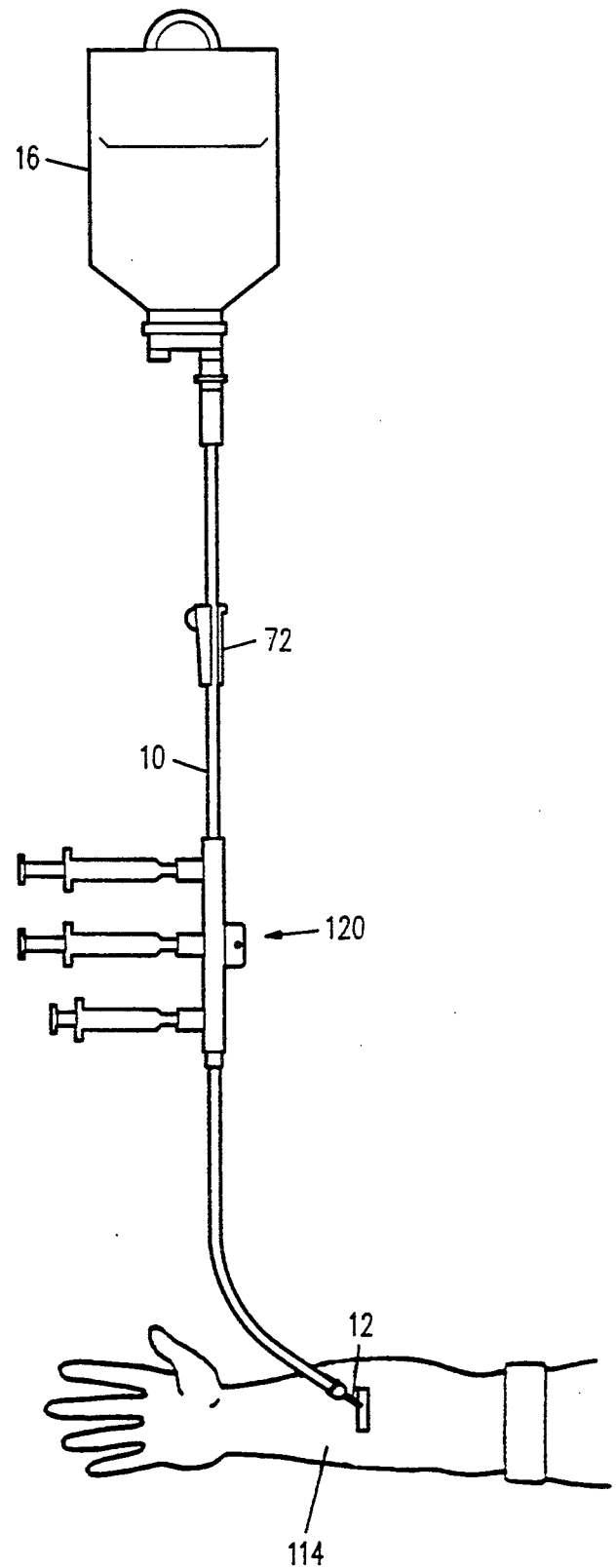
FIG. 4 is a schematic view of another embodiment of the parenteral fluid injector of the present invention for use with an IV line.

Referring to FIG. 4, there is shown another embodiment of an injector 120 of the present invention. The injector 120 is shown connected to an IV line 10 with a needle 12 or IV catheter 12 at one end connected to a patient 114. Another end of the IV line 10 is a source of fluid, such as glucose. The injector 120 is placed "in-line" with the IV line 10 with luer connectors or it may be built into an IV set.

Figure 5:
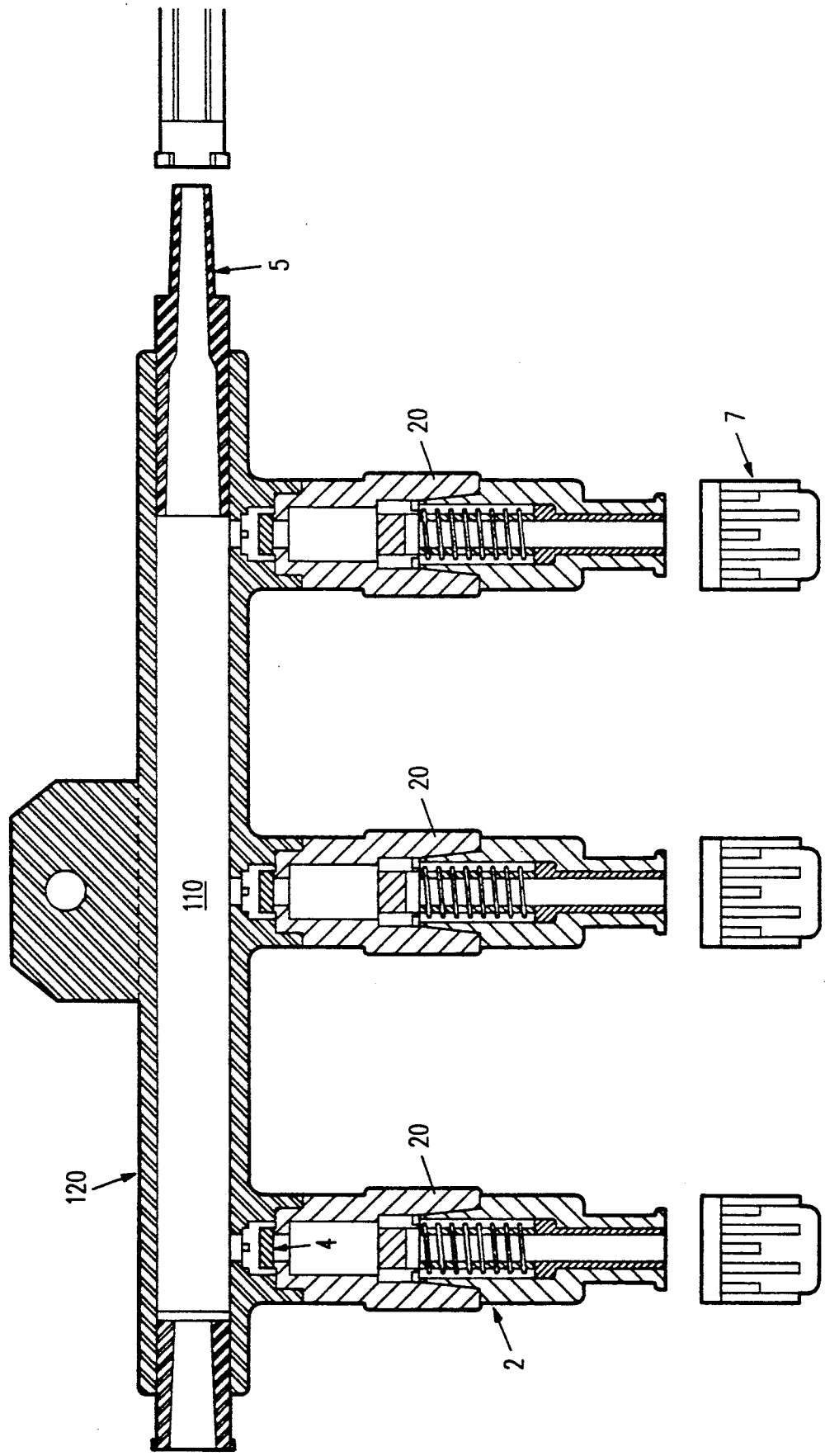
FIG. 5 is a cross-sectional view of the parenteral fluid injector shown in FIG. 4.

Referring to FIG. 5, there is shown a cross-sectional view of the injector 120. The injector 120 comprises a plurality of injectors 20 all as shown and described in FIG. 2 connected in tandem to a fluid flow line 110. The fluid flow line 110 may be thought of as simply as another part of the IV line 10. The operation of each of the injectors 20 shown in the injector 120 is identical to that shown and described in FIG. 2. The advantages of the injector 120 is that a plurality of syringes 26, or other IV lines 28 (FIG. 1b), or a combination of such, containing different medications or IV fluids (blood, plasma, antibiotic drips) can be connected "on-line" and be available for instantaneous and intermittent delivery thereof to the patient 114. In many surgical procedures, it is often desirable and necessary to administer a plurality of different drugs or different fluids "on demand". Thus, the injector 120 of the present invention provides this capability with all the attending advantages of safety to the patient as previously described.

What is claimed is:

1. A parenteral fluid and medication injector for use with a fluid transport means having one end for connection to a patient and a fluid input port for receiving a fluid or medication, wherein the improvement comprising:

a fluid conduit having two ends; a first end for receiving said fluid or medication, and a second end having means for connecting to said fluid input port of said fluid transport means for dispensing said fluid or medication into said fluid transport means;

a first valve means, located at said second end of said fluid conduit, for preventing backflow of said fluid or medication from the second end of said fluid conduit to the first end;

a second valve means comprising:

an injection piston in said fluid conduit, located at said first end of said fluid conduit, movable between a first position and a second position;

said piston having a central bore for the passage of said fluid; said piston having a capped end and an injection inlet port, and an envelope space surrounding said piston interior to said fluid conduit, and between said capped end and said injection inlet port, said envelope space fluidically connected to said inlet port;

spring urging means for urging said piston in said first position;

sealing means between said piston and said fluid conduit at said capped end for sealing said fluid flow between said inlet port and said fluid transport means, when said piston is in said first position; and means for permitting fluid flow between said inlet port and said fluid transport when said piston is in said second position.

2. The injector of claim 1 wherein said first valve means is a member movable under fluid pressure alone, between a first position, wherein fluid cannot flow in said conduit between said two ends, and a second position, wherein fluid can flow between said two ends.

3. The injector of claim 2 wherein said member has a specific gravity greater than 1.0.

4. The injector of claim 1 wherein said sealing means is an o-ring.

5. The injector of claim 4 further comprising:

a washer between said o-ring and said spring urging means.

6. The injector of claim 5 wherein said o-ring has an outer diameter smaller than the diameter of said fluid conduit and an inner diameter substantially smaller than the diameter of said piston.

7. The injector of claim 6 wherein said spring urging means is a stainless steel spring in said envelope, surrounding said piston.

8. The injector of claim 1 wherein said fluid transport means has a plurality of input ports.

9. The injector of claim 8 further comprising a plurality of said fluid conduits, each fluid conduit connected to one of said fluid input ports of said fluid transport means, each fluid conduit comprising said first valve means and said second valve means.

10. The injector of claim 9 wherein each of said second valve means further comprising:

an injection piston in said fluid conduit, located at said first end of said fluid conduit, movable between a first position and a second position;

said piston having a central bore for the passage of said fluid; said piston having a capped end and an injection inlet port, and an envelope surrounding said piston interior to said fluid conduit, and between said capped end and said injection inlet port;

spring urging means for urging said piston in said first position;

sealing means between said piston and said fluid conduit at said capped end for sealing said fluid flow and preventing any air flow between said inlet port and said fluid transport means, when said piston is in said first position;

means for permitting fluid flow between said inlet port and said fluid transport when said piston is in said second position; and means for permitting fluid flow between said inlet port and said envelope.

11. The injector of claim 10 wherein said first valve means is a member movable under fluid pressure alone, between a first position, wherein fluid cannot flow in said conduit between said two ends, and a second position, wherein fluid can flow between said two ends.

12. The injector of claim 11 wherein said member has a specific gravity grater than 1.0.

13. The injector of claim 12 wherein said sealing means is an o-ring.

14. The injector of claim 13 further comprising:
a washer between said o-ring and said spring urging means.

15. The injector of claim 14 wherein said o-ring has an outer diameter smaller than the diameter of said fluid conduit and an inner diameter substantially smaller than the diameter of said piston.

16. The injector of claim 15 wherein said spring urging means is a stainless steel spring in said envelope, surrounding said piston.

17. A parenteral fluid and medication injector for use with a fluid transport means having one end for connection to a patient and a fluid input port for receiving a fluid or medication diluted by a diluting fluid, forming a diluted fluid, said injector comprising:
- a first port for connecting to said fluid input port and for dispensing said diluted fluid;
- a second port for receiving said diluting fluid;
- a third port for receiving said fluid or medication;
- a first fluid conduit connecting said first, second and third ports;
- injection means connected to said third port; said injection means comprising
  - a second fluid conduit having two ends; a first end for receiving said fluid or medication, and a second end having means for connecting to said third port for dispensing said fluid medication;
  - a first valve means, located at said second end of said second fluid conduit, for preventing backflow of said diluted fluid to the first end;
  - a second valve means, located at said first end of said second fluid conduit, for preventing air embolus in said second fluid conduit, and for receiving said fluid or medication for injection into said fluid transport means, said second valve means further comprising:
    - an injection piston in said second fluid conduit, located at said first end of said second fluid conduit, movable between a first position and a second position;
    - said piston having a central bore for the passage of said fluid; said piston having a capped end and an injection inlet port, and an envelope space surrounding said piston interior to said second fluid conduit, and between said capped end and said injection inlet port, said envelope space fluidically connected to said inlet port;
    - spring urging means for urging said piston in said first position;
    - sealing means between said piston and said second fluid conduit at said capped end for sealing said fluid flow and preventing any air flow between said inlet port and said fluid transport means, when said piston is in said first position; and
    - means for permitting fluid flow between said inlet port and said fluid transport when said piston is in said second position.

* * * * *